United States Patent [19]

Goldstein et al.

[11] Patent Number: 4,482,577

[45] Date of Patent: Nov. 13, 1984

[54] COATING PROCESS OF ELASTOMERIC MATERIAL

[76] Inventors: Albert Goldstein, Glenwood Ave., Tinton Falls, N.J. 07724; Howard I. Podell, 28 Beachfront La., New Rochelle, N.Y. 10805

[21] Appl. No.: 216,889

[22] Filed: Dec. 16, 1980

[51] Int. Cl.$^3$ .......................... A61B 19/04; B05D 3/10
[52] U.S. Cl. ........................................ 427/2; 427/307; 427/322; 427/385.5; 427/393.5; 427/430.1
[58] Field of Search ............... 427/2, 322, 307, 430.1, 427/393.5, 385.5, 444; 2/168; 260/31.2 R; 156/668

[56] References Cited

U.S. PATENT DOCUMENTS

| | | | |
|---|---|---|---|
| 2,400,720 | 5/1946 | Staudinger et al. | 156/646 |
| 2,976,576 | 3/1961 | Wichterle et al. | 128/156 |
| 3,142,581 | 7/1964 | Leland | 427/304 |
| 3,445,264 | 5/1969 | Haines | 427/306 |
| 3,503,942 | 3/1970 | Seiderman | 526/320 |
| 3,762,978 | 10/1973 | Holmes et al. | 427/322 |
| 3,784,540 | 1/1974 | Kliment et al. | 260/31.2 R |
| 3,813,695 | 6/1974 | Podell et al. | 2/168 |
| 3,852,826 | 12/1974 | Schindler | 2/168 |
| 3,869,303 | 3/1975 | Orlov et al. | 427/444 |
| 4,024,317 | 5/1977 | Stoye et al. | 427/322 |
| 4,039,714 | 8/1977 | Roubal et al. | 427/307 |
| 4,082,862 | 4/1978 | Esemplar | 2/168 |
| 4,086,852 | 5/1978 | Hamermesh et al. | 427/307 |
| 4,144,363 | 3/1979 | Balloni et al. | 427/322 |
| 4,170,582 | 10/1979 | Mori et al. | 526/320 |

FOREIGN PATENT DOCUMENTS

| | | | |
|---|---|---|---|
| 208084 | 7/1956 | United Kingdom | 427/307 |
| 859297 | 1/1961 | United Kingdom | 526/320 |
| 1028446 | 5/1966 | United Kingdom | 526/320 |

*Primary Examiner*—Norman Morgenstern
*Assistant Examiner*—Janyce A. Bell

[57] ABSTRACT

A treatment of a shaped flexible elastomer item so as to form a coating of a hydrophilic polymer on the surface of the elastomer. The treatment encompasses cleaning of the elastomer surface, immersion of the elastomer in a concentrated solution of a strong acid such as sulphuric acid, washing, and subsequent dipping of the treated elastomer in a solution of an uncured hydrophilic polymer. The treated elastomer is then held at an elevated temperature for a period of time to cure the polymer coating and to bond the polymer coating to the elastomer.

2 Claims, No Drawings

COATING PROCESS OF ELASTOMERIC MATERIAL

STATEMENT OF PRIOR ART

Prior processes for coating flexible rubber elastomers with a hydrophilic polymer have disclosed the process of immersing elastomers in the shape of bathing caps or catheters in a casting solution of a hydrophilic hydrogen polymers. It has also been known that the polymer will bond to the elastomer when the surface of the elastomer has been treated with a halogenating agent.

Other processes of interest for treatment of coating of elastomer surfaces included the following U.S. patents:
U.S. Pat. No. 3,966,530
U.S. Pat. No. 3,925,138
U.S. Pat. No. 4,152,477
U.S. Pat. No. 3,326,742
U.S. Pat. No. 3,745,042
U.S. Pat. No. 3,930,076
U.S. Pat. No. 4,024,317
U.S. Pat. No. 4,110,495
U.S. Pat. No. 3,813,695 discloses a surgeon's glove which has been coated with a layer of hydrophilic polymer, so as to provide improved slip on the inner surface of the glove together with providing perspiration absorption properties of the coating.

SUMMARY OF THE INVENTION

This invention comprises an improved treatment of a flexible shaped elastomer item so as to form an external coating of a hydrophilic polymer on a surface of the elastomer. The treatment encompasses cleaning of the elastomer surface, immersion of the elastomer in a concentrated solution of a strong non-halogen acid such as sulphuric acid, washing, and subsequent dipping of the treated elastomer in a solution of an uncured hydrophilic polymer. The treated elastomer is then held at an elevated temperature for a period of time to cure the polymer coating and to bond the polymer coating to the elastomer.

BACKGROUND OF THE INVENTION

Articles formed of rubber or latex rubber compounds have been coated with hydrophilic polymers for the purpose of providing a hydrophilic surface to the article. The known coating treatment for such products include pre-treatments of the rubber or latex which may degrade the properties of the substrate later or rubber. Such pre-treatments include the application of halogenating agents to the elastomer substrate to improve the bonding of the coating to the elastomer substrate.

An aim of this invention has been the development of an improved process for the coating of a flexible vulcanized rubber article, such as a surgeon's glove, by forming a lamination of a hydrophilic polymer, so that the external lamination of the coating of the polymer will eliminate the need for lubricating powder on the glove. Such surgeon's gloves are normally fabricated by vulcanizing, under heat, a latex rubber compound which has been applied on a ceramic mandrel with subsequent removal of the vulcanized glove from the mandrel or mold. The vulcanized latex rubber of conventional surgeon's glove may be stretched to approximately 700% of its normal length before elastic failure under tension and such flexibility is highly desired.

An important aspect of the process of the invention lies in the prevention of degradation of the elastomer substrate by control of the time of dipping of the glove in the acid solution and or the control of the temperature of the acid solution. It has been found that a typical surgeon's glove will lose a high degree of flexibility, if it is immersed in a concentrated solution of acid such as sulphuric acid for as much as a period of ten seconds or more, where the acid is at an ambient temperature of 17° C. to 23° C. As described hereinafter, we have limited the total elapsed time of our process, from initial starting to dip the glove in the sulfuric acid solution to final immersion in a water rinse solution, to less than ten seconds. Such gloves, when dipped in the concentrated acid at the ambient temperature described will be noticeably stiffer than an untreated glove, but will sufficiently flexible for normal use. However, we have eliminated any noticeable stiffening of the treated elastomer when we have lowered the temperature of the sulphuric acid to below 0° C. and limited the total immersion time in the cooled acid to less than ten seconds. Test samples of surgeons' gloves examined ten months after processing have shown that there has been no loss of elasticity or tensile strength during that period of time after treatment with the concentrated sulfuric acid solution as described above.

DESCRIPTION OF THE PREFERRED EMBODIMENT

The following description is of a process actually employed by the inventors' treating and coating previously finished vulcanized latex surgeon's gloves.

Finished vulcanized surgeon's latex rubber gloves are washed in a hot soap and water solution to remove any powder and other surface contaminants. Each glove is then manually mounted on a clean ceramic mandrel with the exterior surface of the mounted glove being the normal internal glove surface of use.

The glove mandrel, held in the finger down position, is then quickly dipped, for substantially the length of mandrel covered by the glove, into a container of concentrated sulphuric acid of a general concentration of 95%–100% acid. The glove mandrel is then removed from the container and the dipped length is immediately immersed in a first rinse container of water and after a few seconds, removed and immersed in a second rinse container of water or subjected to a wash from a supply of frest water. A quantity of a dilute basic solution, such as ammonium hydroxide may be added to the first or second rinse container to neutralize any acid carried over from the acid dip stage.

The glove is then dried on the mandrel, preferably at a temperature of less than 90° C. in an oven for a few minutes and the dipped length of mandrel is then inserted into a dilute polymer coating solution for less than one minute. The time of immersion in the coating solution is not critical, but the mandrel is preferably removed from the coating solution at a slow rate so as to permit most of the excess polymer to flow downwards from the glove as the mandrel is removed from the coating solution. The mandrel may be manually agitated to remove any drops of coating and preferably the mandrel is manually rotated during the initial stage of drying of the coating so as to provide for uniformity of thickness of the dried coating. The mandrel, after drying, is then heated in an oven for a period of twenty to thirty minutes at an oven temperature of approximately 105° C. to 125° C.

After the mandrel has been removed from the oven and allowed to cool, the glove is stripped from the mandrel, preferably under a spray of water, or with the glove and mandrel held in a container of water. The glove, while wet is then rinsed in a dilute dispersion of dimethyl polysiloxane so as to apply non-tacky surface to the uncoated side of the glove, after which rinse, the glove is again rinsed in water and allowed to dry.

The finished gloves, when dry, are reversed so that the coated side is now the interior glove surface. The coating of hydrophilic polymer forms a smooth slip surface which adheres to the latex rubber substrate of the glove, enven when the glove is stretched, and enables a user to readily don the glove without the use of any other lubricants or powder material.

The following polymer coating solution has been utilized. This polymer coating solution and its preparation is described in a separate U.S. patent application Ser. No. 216,890 filed on Dec. 16, 1980 at the same time as the filing of this application by one of the present co-inventors.

COATING SOLUTION TYPE A

Coating solution, Type A, is preferably utilized in concentrations of one (1) to four (4) percent of weight, and preferably at a concentration of two (2) percent by weight of a copolymer in a solution of an organic solvent such as methoxyethanol or ehtanol. The copolymer is produced from a mixture of 80 parts (by weight) of 2-Hydroxyethyl Methacrylate
20 parts (by weight) of 2-Ethyl-hexyl Acrylate To the polymer solution is added a catalyst and or curing agent consisting of Dicyclopentadiene Diepoxide in the ratio of 0.004 grams per gram of polymer in the solution (0.4 phr) and Para Toluene Sulfonic Acid Monohydrate in the ratio of 0.1 phr. Alternatively a curing agent of 0.4 phr of Ammonium Dichromato may be employed in the polymer solution.

An alternative pre-treatment for the gloves, instead of the dip in the concentrated sulfuric acid, is a dip in a 2% to 4% dilute solution of Polyethyleneimine (PEI) in 2-methoxyethanol.

The increased concentration of coating solution generally results in a thicker coating for a given set of conditions. The tiem of dip in the coating solution is not critical, but it is desirable to rotate the glove and mandrel along different axes after removing the mandrel from the coating solution so as to achieve a uniform thickness of dried coating.

After the coating has been cured in the oven, the gloves are preferably stripped from the mandrel under a spray of water or a spray of a dilute solution (0.1% to 1%) of dispersion of dimethylpolysiloxane in water. Tis spray reduces self-adhesion of the uncoated side of the glove as it is removed and reduces the tackiness of the uncoated surface. The gloves may be finally washed in water to remove excess dispersion.

Since obvious changes may be made in the specific embodiment of the invention described herein, such modifications being within the spirit and scope of the invention claimed, it is indicated that all matter contained herein is intended as illustrative and not as limiting in scope.

Having thus described the invention, what I claim as new and desire to secure by Letters Patent of the United States is:

1. A method of coating of a vulcanized latex rubber product, so as to coat a surface of the product with a hydrophilic poylmer comprising the following steps:
    (1) Clean the product surface by washing;
    (2) Immerse the product into a treatment solution of highly concentrated sulfuric acid solution of a concentration of at least substantially 95% concentration of sulfuric acid;
    (3) Remove the product from the said treatment solution;
    (4) Wash the product surface;
    (5) Immerse the product into a coating solution of a hydrophilic polymer;
    (6) Remove the product from the coating solution; and
    (7) Heat the coated product for a period of time; in which the said treatment solution of sulfuric acid is maintained at a temperature substantially below seventeen degrees Celsius so as to minimize a stiffening effect to the latex rubber product otherwise resulting from the action of the treatment solution on the said product.

2. The method as described in claim 1, in which said treatment solution is maintained at a temperature below zero, degrees celsus.

* * * * *